United States Patent [19]

Shaftel

[11] Patent Number: 4,617,511
[45] Date of Patent: Oct. 14, 1986

[54] ELECTRODE PROBE ASSEMBLY FOR GLASS LINED METAL VESSELS

[75] Inventor: Myles A. Shaftel, Rochester, N.Y.

[73] Assignee: Kennecott Corporation, Cleveland, Ohio

[21] Appl. No.: 764,505

[22] Filed: Aug. 8, 1985

Related U.S. Application Data

[63] Continuation of Ser. No. 644,133, Aug. 23, 1984, abandoned, which is a continuation of Ser. No. 387,915, Jun. 14, 1982, abandoned, which is a continuation of Ser. No. 135,671, Mar. 31, 1980, abandoned.

[51] Int. Cl.$^4$ .................. G01R 31/12; G01R 27/02; G01N 27/28
[52] U.S. Cl. ...................................... 324/54; 324/65 P; 324/450
[58] Field of Search .............. 324/446, 447, 448, 450, 324/52, 54, 65 P, 65 CP, 158 P

[56] References Cited

U.S. PATENT DOCUMENTS

| | | | |
|---|---|---|---|
| 2,824,282 | 2/1958 | Posey | 324/446 |
| 3,418,848 | 12/1968 | Schaschl | 324/65 CR |
| 3,944,916 | 3/1976 | Tillander | 324/65 P |

Primary Examiner—Ernest F. Karlsen
Assistant Examiner—Walter E. Snow
Attorney, Agent, or Firm—R. Lawrence Sahr

[57] ABSTRACT

An electrode probe assembly for monitoring and finding fault in the glass lining of metal vessels, pipes or the like, characterized by a cup-shaped electrode with an insulated stud inserted through a hole in the wall of a mounting member. An insulating gasket insulates the electrode from the member. Resilient means bias the cup-shape electrode against the gasket preventing leakage due to shrinkage of the gasket. Electrical connection of an insulated circuit is made to the stud.

5 Claims, 7 Drawing Figures

ELECTRODE PROBE ASSEMBLY FOR GLASS LINED METAL VESSELS

This application is a continuation of application Ser. No. 644,133 filed Aug. 23, 1984, now abandoned, which in turn was a continuation of application Ser. No. 387,915 filed June 14, 1982, now abandoned, which in turn was a continuation of application Ser. No. 135,671 filed Mar. 31, 1980, also now abandoned.

BACKGROUND OF THE INVENTION AND PRIOR ART

This invention pertains to electrical testing of protective linings of steel pipes, vessels, and other liquid containers, and is more particularly concerned with the structure of an electrode probe assembly for performing such tests.

Steel containers such as vessels and pipes are widely used in the food and chemical industries for processing liquids. A protective lining of material such as glass, plastic, or rubber is often required to separate the steel shell of the container from the corrosive effect of the liquid. It is important that the lining be free of defects or faults because if contact were to be made between liquid and shell, the steel would corrode and possibly result in the failure of the steel container. Also, corroded steel particles would contaminate the liquid product.

For those reasons electrical fault finders have been used for detection of defective linings, eliminating unexpected, possibly catastrophic, vessel failures and allowing the transfer of the liquid product to another vessel before iron contamination becomes critical. In either case, repairs to the lining can be made before permanent, irreparable damage results.

An intact lining functions as an electrical insulator between the conductive liquid product and the steel. This property can be utilized in testing for defects.

One approach to detect faults in the lining is to actively impress a voltage between an electrode immersed in the conductive liquid and the steel shell which contains the liquid. Current flow indicates a defect in the lining. Alternatively, passive galvanic fault finders may be used.

Galvanic fault finders operate on the principle that dissimilar metals electrically connected together and immersed in a conductive liquid (electrolyte) develop a voltage between the metals. The galvanic fault finder detects this voltage or the current produced. U.S. Pat. Nos. 3,831,058 and 3,858,114 describe an arrangement wherein a platinum electrode is immersed in the electrolyte liquid contents of a lined steel vessel. The platinum electrode must be electrically insulated from the steel shell. If the liquid contents of the vessel or pipe makes contact with the steel shell a voltage occurs between shell and electrode. Monitoring this voltage or the resultant current provides indication of a fault.

A significant difficulty with the typical probe assemblies of the prior art (exemplified in FIG. 3) is leakage and/or breakage of the electrode which is made from tantalum alloy. This material is very brittle and overtightening the electrode easily causes breakage. The acceptable tightening torque is very low. Also, when the electrode is installed, a polytetrafluoroethylene (PTFE) gasket is compressed to make a liquid-tight seal. However, if the electrode has sharp edges, the electrode may cut through the gasket as it is screwed in. Another problem is the relaxation of the PTFE gasket over time and temperature. Both difficulties result in possible leakage of the probe installation.

An object of the invention is to provide a fault finding electrode completely isolated from conduction members such as flush valve assemblies or baffles.

Another object of the invention is to provide an electrode assembly having an electrical circuit which is immune to corrosive humidity and water.

Another object of the invention is to provide an electrode assembly that does not cut a sealing gasket.

A further object of the invention between an electrode is to maintain a liquid-tight seal assembly and its mounting member even if the gasket relaxes.

SUMMARY OF THE INVENTION

An electrode probe assembly is provided for finding faults in the glass lining of a liquid containing metal vessel. An electrode in the form of a cup threaded onto an insulated stud is mounted over an aperture through the wall of the vessel. Resilient means are fitted on the stud on the exterior side of the wall to pull/bias the electrode against the gasket. Electrical connection is made to the stud.

DESCRIPTION OF THE INVENTION

It will be seen that the electrode probe of the present invention is, in contrast to the closest prior art, completely electrically isolated from the mounting member through which it is mounted, and from the wall or shell of the vessel, pipe, or other liquid vessel in which it is used. Furthermore, the probe has an insulated electric circuit leading from the electrode 1 to outside the container. This circuit is immune to corrosion, humidity and water. The electrode probe includes a sealing gasket 7 to make a liquid tight seal which is maintained even if the sealing gasket 7 relaxes somewhat after installation.

Figure 1:
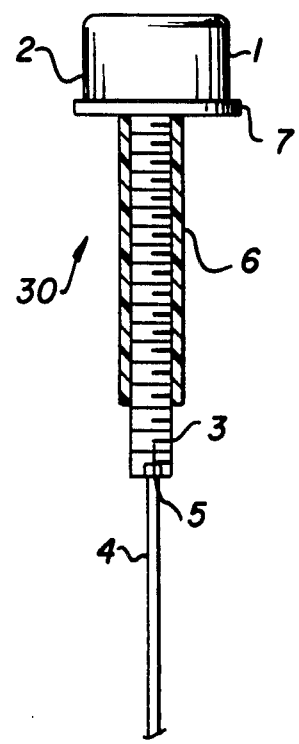
FIG. 1 shows an electrode subassembly as a component of the probe of the present invention.

Reference is made to FIG. 1 which represents the electrode subassembly 30 of the probe. The active portion of the electrode 1 is preferably platinum. Because of the high cost of platinum preferably only a thin layer of platinum is applied to another metal, for example an inert alloy of tantalum. For the purpose of this description, and in the claims, the electrode 1 includes the entire piece of platinum plated metal.

The present invention allows an improvement in the mechanical function of the electrode 1. In the closest prior art, the electrode was installed as a screw which was screwed into the steel of a member required to be electrically isolated from the vessel. As a feature of the invention, the electrode 1 may be in the form of a nut which is intrinsically much stronger than a blind screw.

The underside of the blind nut electrode is drilled, but not through, and tapped. Drilling and tapping tantalum is difficult. For this invention, though, a good quality internal thread is not a necessity. The thread quality need only be adequate to screw in and bottom a socket set screw 3. The design allows for reasonably loose tolerances and the use of a coarse thread set screw 3. The coarse thread eliminates the chance of crossthreading.

Figure 7:
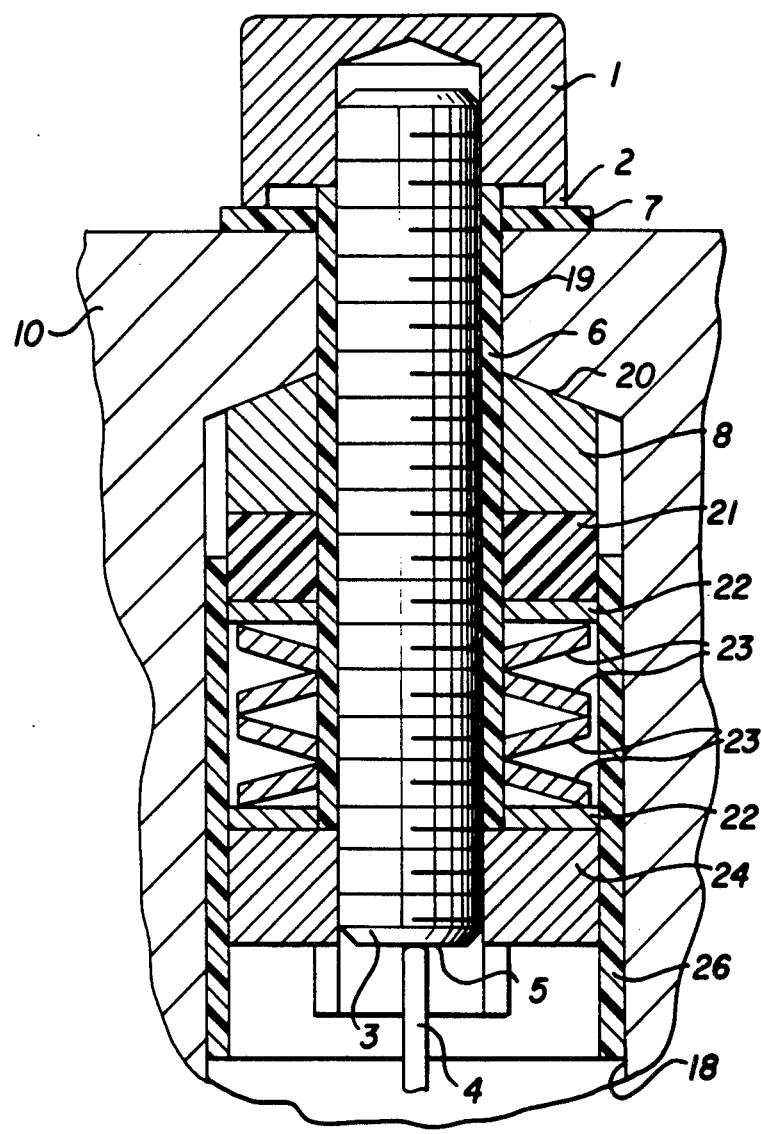
FIG. 7 represents an enlarged sectional view of FIG. 2 fully cut away to further disclose the elements of the present invention.

As seen in FIG. 7 socket head set screw 3 is screwed into the electrode 1. In contrast with the prior art, exemplified in FIG. 3, the threaded portion of the electrode 1 need not be tantalum alloy, but may be hardened steel. The prior art tantalum threaded portion (seen in FIG. 3) easily broke off because of the brittleness of tantalum.

It is also difficult to solder or weld to tantalum because of the material's high temperature properties. In the preferred embodiment a PTFE coated wire 4 is soldered in socket 5 or otherwise affixed to the set screw 3 making a reliable electrical connection to the electrode 1. Thus, screw 3 functions as both a mounting stud and electrical connection to the electrode 1.

The set screw 3 is insulated for most of its length by means of heat shrinkable tubing 6. A PTFE gasket 7 is slipped over the set screw 3 and pushed against the underside of the electrode 1. In keeping with the invention, the electrode 1 is provided with a sealing lip 2. The tubing 6 and gasket 7 provide electrical insulation from the steel member in which the probe is mounted.

Figure 4:
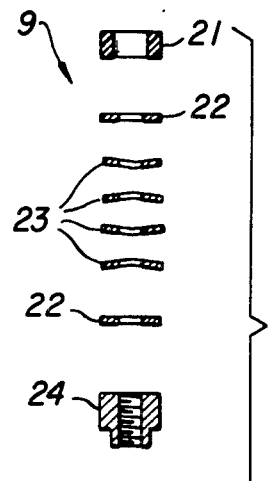
FIG. 4 shows an exploded view of a probe subassembly seen in assembled form in FIGS. 2 and 3 and 7.

The electrode probe is made up of the insulated electrode subassembly 30 described above, a beveled hub 8, and a probe subassembly 9 which is seen in detail in FIG. 4.

The function of the latter items are best explained in the context of a probe assembled in a vessel or pipe mounting member. A drain valve is used as an example of a mounting member. An assembled probe in a valve head is seen in FIG. 2 and may be compared with the prior art probe of FIG. 3.

Figure 2:
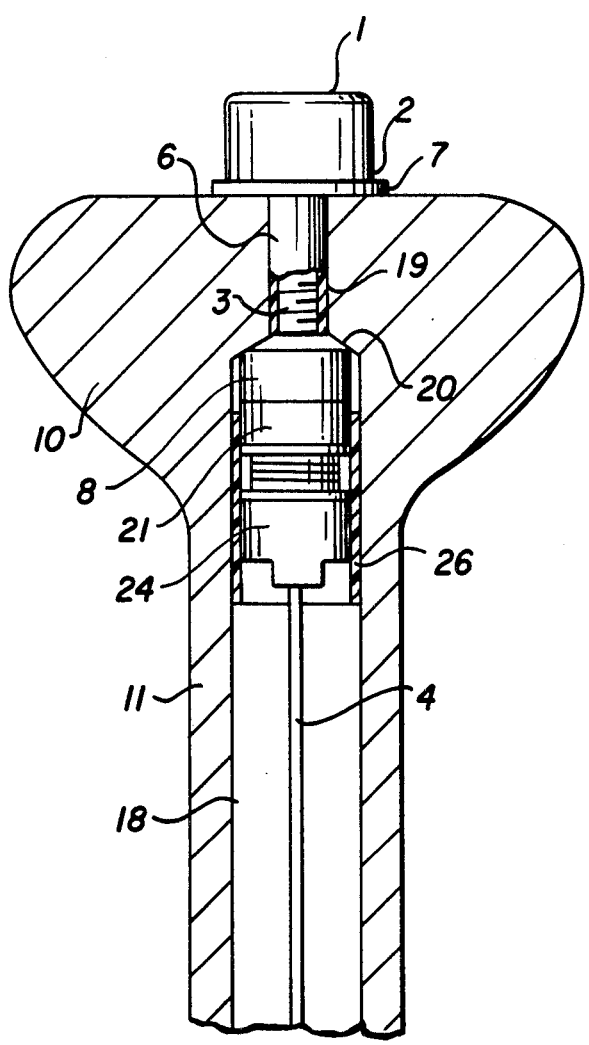
FIG. 2 shows a complete probe assembly mounted in a mounting member.
Figure 3:
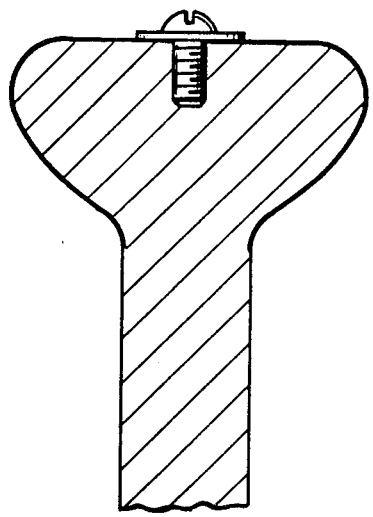
FIG. 3 shows a probe of the prior art mounted in a valve head, as a representative mounting member, in contrast with the probe of FIG. 2.

The valve heads FIGS. 2 and 3 are identical except for modifications to accept the improved electrode assembly. A valve head 10 and valve stem 11 are fabricated in one piece from steel and has a layer of insulating material such as glass.

Referring specifically to the improved arrangement of FIG. 2, it is seen that the valve stem 11 is drilled along the length of its axis with this first bore 18 terminating within the valve head 10.

A second, smaller diameter bore 19 is drilled along the axis and through the valve head to meet the first bore 18 at junction 20. A diamond tip bit may be required to penetrate the glass layers for the second bore 19. The junction 20 of the two bores 18, 19 is beveled to the same angle as the bit used for drilling the first bore 18.

The electrode subassembly FIG. 1 is fitted on the valve head 10 with the set screw 3 inserted in the smaller diameter second bore 19 and extending into the larger diameter first bore 18.

A hub 8 is beveled on one side to conform to the bevel 20. The other side provides a flat surface for the probe subassembly 9 to press against. The hub 8 is installed over the set screw 3 protruding into the first bore 18. The shrink tubing 6 on the set screw and the PTFE gasket 7 provide electrical insulation between the screw 3 and the steel of both the valve head and the beveled hub 8. The gasket is compressed by the sealing lip of the electrode to prevent liquid from reaching the steel of the mounting member through which the probe is mounted.

The probe subassembly 9, FIG. 4, includes, in order, an insulating ceramic washer 21, a plurality of metal flat washers 22, a plurality of disc springs 23 and a securing nut 24 having a thread matching that of the stud 3. The elements of the probe subassembly 9 are held together by a piece of PTFE shrink tubing 26. The tubing 26 insulates the subassembly 9 from the metal of the mounting member.

Figure 5:
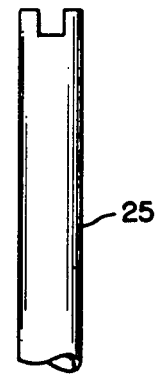
FIG. 5 illustrates a wrench suitable for assembling the probe assembly.

During assembly of the probe the nut 24 is tightened by an extending hollow wrench 25 such as shown in FIG. 5. The probe subassembly 9 is placed on the wrench and slipped over the electrode wire 4 and inserted up the first bore 18. The electrode subassembly 30 is held stationary to prevent rotation and nut 24 of the probe subassembly 9 is screwed onto the stud 3 thereby sealing gasket 7.

If the gasket relaxes 7, due to cold-flowing, the disc springs 23 compensate for the amount of relaxation maintaining a liquid-tight seal. Because the electrode 1 is held stationary during installation, the gasket 7 is not cut. The ceramic insulating 21 washer electrically insulates the metal washers 22 from the hub.

The electrode wire 4 continues down the first bore 18. Transition is made to armored cable for connection to instrumation.

The electrode probe is not limited to valves, but may be mounted on a variety of mounting members in both vessels and pipes. Because the probe is self insulating there is no need to insulate the member from the rest of the structure or from ground.

Figure 6:
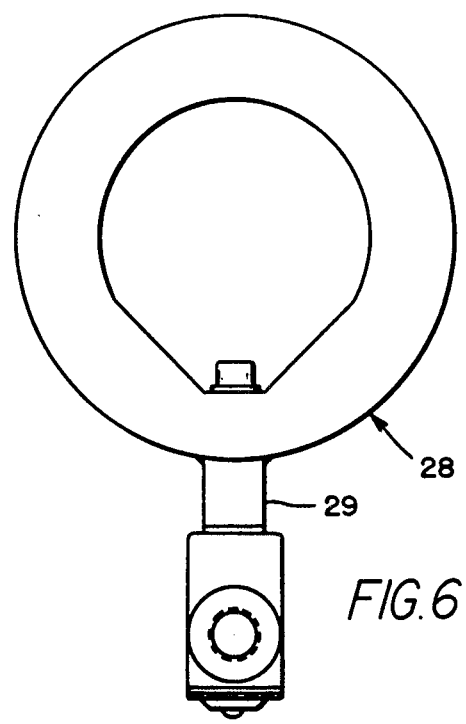
FIG. 6 represents a pipe spacer, as an example of another member upon which the probe may be assembled.

In FIG. 6 of the drawings, the probe is seen mounted in a pipe spacer 28. A rod 29 is radially attached on the side of the spacer and bores are provided in the spacer and tube for the probe. Otherwise, the arrangement is the same as used in the valve stem, and need not be described further. Other possible members include baffles and blind flanges.

The invention improves markedly the performance and reliability of the earlier fault detection probe assemblies used for many years. Parts other than the electrode are located inside the member and are protected from environmental factors and subsequent degradation. The probe assembly is therefore immune from the effects of moisture, dirt and breakage. It maintains a leak-tight seal up to the limits of the gasket material. The function of the fault detection system is not hindered or degraded in any way, by the improved structure but is more reliable and trustworthy than the closest prior art.

I claim:
1. An electrode probe assembly for use with a metal vessel having a glass lined inner wall surface, comprising:
   (a) an electrode formed from a blind metal nut, platinum plated, and having an internal screw threaded aperture extending into but not through said nut;
   (b) a lip member extending from the periphery of said nut and from that face of said nut into which said aperture extends, forming a cup of the combination of said nut and said lip member;
   (c) an elongated threaded metal stud having a first end threaded into said internal screw thread of said aperture; said stud being adapted to extend through a bore in a mounting member for said electrode probe assembly;

(d) an insulating gasket disposed around said stud, adapted to be positioned between said lip member and an adjacent surface of said mounting member;

(e) a hub means disposed around said stud, having a butress surface adapted to butress against an opposed surface of said mounting member, said opposed surface which is located remote from said adjacent surface of said mounting member;

(f) insulation washer means, disposed around said stud, positioned against said hub means and located remote from said butress surface of said hub means, adapted to electrically insulate and separate said hub means from;

(g) resilient biasing means, disposed around said stud, adapted to continuously exert pressure linearly along the axis of said stud to force said hub means along said axis of said stud towards said insulating gasket and said nut and to urge said lip member towards said insulating gasket when said electrode probe assembly is mounted in said mounting member;

(h) insulating tube means disposed around said stud, adapted to electrically insulate and separate said stud from said mounting member, said hub means, said insulation washer means and said resilient biasing means;

(i) insulating sleeve means, disposed around said resilient biasing means, adapted to electrically insulate and separate said resilient biasing means from said mounting member; and (j) means, mounted to the second end of said stud, for electrically connecting said stud to an electrical circuit.

2. The invention of claim 1 wherein said resilient biasing means comprises a plurality of disc springs positioned to exert linear force on said insulation washer means.

3. The invention of claim 1 wherein said resilient biasing means includes a securing nut means threaded onto and positioned adjacent to said second end of said set screw, adapted to secure said resilient biasing means to said electrode probe assembly.

4. The invention of claim 2 wherein said resilient biasing means includes a securing nut means threaded onto and positioned adjacent to said second end of said set screw, adapted to secure said plurality of disc springs in position to exert linear force on said insulation washer means.

5. The invention of claim 4 further comprising a plurality of flat washer means interposed to separate said plurality of disc springs from said insulation washer means and said securing nut means.

* * * * *